United States Patent
Spadgenske et al.

(10) Patent No.: US 11,918,821 B2
(45) Date of Patent: Mar. 5, 2024

(54) CONNECTOR FOR USE IN OVERMOLDED HEADER OF IMPLANTABLE PULSE GENERATOR

(71) Applicant: Cardiac Pacemakers, Inc., St. Paul, MN (US)

(72) Inventors: Scott A. Spadgenske, Buffalo, MN (US); James Michael English, Cahir (IE); Trey Henry Achterhoff, St. Paul, MN (US); Robert Allen Jones, Lake Elmo, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 136 days.

(21) Appl. No.: 17/125,018

(22) Filed: Dec. 17, 2020

(65) Prior Publication Data
US 2021/0187306 A1  Jun. 24, 2021

Related U.S. Application Data

(60) Provisional application No. 62/950,782, filed on Dec. 19, 2019.

(51) Int. Cl.
*A61N 1/375* (2006.01)

(52) U.S. Cl.
CPC ....... *A61N 1/3752* (2013.01); *A61N 1/37512* (2017.08)

(58) Field of Classification Search
CPC . A61N 1/3752; A61N 1/37512; A61N 1/3754
See application file for complete search history.

(56) References Cited

U.S. PATENT DOCUMENTS

| | | | | |
|---|---|---|---|---|
| 7,601,033 B2* | 10/2009 | Ries | ..................... | A61N 1/3752 439/669 |
| 8,096,838 B2* | 1/2012 | Dilmaghanian | ....... | H01R 24/58 439/669 |
| 8,437,855 B2* | 5/2013 | Sjostedt | ................. | H01R 24/58 439/668 |
| 8,480,437 B2* | 7/2013 | Dilmaghanian | ..... | A61N 1/3752 439/669 |
| 8,500,499 B2* | 8/2013 | Drew | ................... | H01R 13/187 439/843 |
| 2003/0073348 A1* | 4/2003 | Ries | ..................... | A61N 1/3752 439/578 |
| 2003/0163171 A1* | 8/2003 | Kast | ....................... | H01R 24/58 607/36 |

(Continued)

OTHER PUBLICATIONS

International Search Report and Written Opinion issued in PCT/US2020/065554, dated Mar. 11, 2021, 26 pages.

*Primary Examiner* — Tammie K Marlen
(74) *Attorney, Agent, or Firm* — Nelson Mullins Riley & Scarborough LLP

(57) ABSTRACT

Various aspects of the present disclosure are directed toward apparatuses, systems, and methods that may include a connector port subassembly. The connector port subassembly may include one or more connector blocks configured to interference fit within a connector bore, one or more windows through the core subassembly to the one or more connector blocks, and one or more seal rings configured to interference fit within the connector bore and eliminate adulterant entry into the connector bore through the one or more windows.

18 Claims, 7 Drawing Sheets

(56) References Cited

U.S. PATENT DOCUMENTS

| | | | | |
|---|---|---|---|---|
| 2008/0139031 A1* | 6/2008 | Ries | ............... | A61N 1/3752 607/116 |
| 2008/0139053 A1* | 6/2008 | Ries | ............... | A61N 1/3752 439/736 |
| 2008/0208278 A1* | 8/2008 | Janzig | ............ | H01R 43/16 607/37 |
| 2008/0246231 A1* | 10/2008 | Sjostedt | ......... | A61N 1/0551 29/428 |
| 2009/0258519 A1* | 10/2009 | Dilmaghanian | ..... | A61N 1/3752 29/877 |
| 2010/0204740 A1* | 8/2010 | Ries | ............... | A61N 1/3752 439/271 |
| 2010/0233896 A1* | 9/2010 | Dilmaghanian | ..... | H01R 13/187 439/669 |
| 2011/0014807 A1* | 1/2011 | Ries | ............... | A61N 1/3752 439/271 |
| 2011/0059639 A1* | 3/2011 | Dilmaghanian | ....... | H01R 24/58 439/271 |
| 2012/0124831 A1* | 5/2012 | Janzig | ............ | H01R 43/16 29/874 |
| 2012/0129409 A1* | 5/2012 | Drew | ............ | A61N 1/3752 219/121.64 |
| 2012/0253443 A1* | 10/2012 | Dilmaghanian | ..... | A61N 1/3752 607/116 |
| 2019/0329048 A1* | 10/2019 | Janzig | ............ | H01R 43/16 |

\* cited by examiner

CONNECTOR FOR USE IN OVERMOLDED HEADER OF IMPLANTABLE PULSE GENERATOR

CROSS REFERENCE TO RELATED APPLICATION

This application claims priority to Provisional Application No. 62/950,782, filed Dec. 19, 2019, which is herein incorporated by reference in its entirety.

TECHNICAL FIELD

The present invention relates to an implantable system having an implantable lead having a connector port. More specifically, the invention relates to a connector port and components arranged within the connector port that allow for adaptability and adjustability in order to comply with various industry connector standards.

BACKGROUND

Implantable medical systems for stimulating a target area or for diagnostic purposes may include different lead configurations that require different industry standards. The systems may include an implantable lead assembly and an implantable pulse generator connected with the implantable lead assembly. The implantable lead assembly may comply with one or more of industry standards (e.g., IS-1, IS4, DF4). Further, a header of the implantable pulse generator generally includes corresponding connector ports that are configured to comply with one or more of the standards so that the implantable lead assembly may be effectively coupled with the implantable pulse generator. A proper connection between the implantable leads and the corresponding connector ports is required to allow proper functioning of the implantable system. In certain instances, a given connector port subassembly may correspond to a single standard. Components used in the connector port subassembly could allow for adaptability and adjustability to reduce the number of required connector port subassemblies.

SUMMARY

In Example 1, a connector port subassembly for a medical device includes a core subassembly; a connector bore arranged within the core subassembly including a proximal end and a distal end; one or more connector blocks configured to interference fit within the connector bore; one or more windows through the core subassembly to the one or more connector blocks; and one or more seal rings configured to interference fit within the connector bore and eliminate adulterant entry into the connector bore through the one or more windows.

In Example 2, the connector port subassembly of Example 1, wherein the one or more seal rings includes sidewalls, a first surface extending between the sidewalls, and a plurality of ridges arranged along the first surface and the sidewalls of the one or more seal rings configured to engage with an interior surface of the connector bore.

In Example 3, the connector port subassembly of Example 2, wherein a diameter of the interior surface of the connector bore is smaller than a diameter of the one or more seal rings.

In Example 4, the connector port subassembly of any one of Examples 2-3, wherein the one or more seal rings includes a first portion comprising a first material, and a second portion comprising a second material, and the first material is less flexible than the second material.

In Example 5, the connector port subassembly of Example 4, wherein the first material includes a high durometer and the second material includes a low durometer.

In Example 6, the connector port subassembly of Example 5, wherein the sidewalls and the first surface of the one or more seal rings comprise the first material.

In Example 7, the connector port subassembly of any one of Examples 1-6, wherein the connector bore includes a terminal pin cavity, and the core subassembly includes a window to the terminal pin and a projection configured to at least partially surround portions of a seal plug.

In Example 8, the connector port subassembly of Example 7, wherein the seal plug is captured within the connector bore producing an interference fit between the seal plug and the connector bore.

In Example 9, the connector port subassembly of any one of Examples 1-8, wherein the one or more seal rings includes two seal rings and the one or more connector blocks includes one connector block, and the two seal rings are arranged on either side of the connector block.

In Example 10, a method of manufacturing one or more connector port subassemblies includes arranging one or more connector blocks within a connector bore to interference fit within the connector bore, the connector bore being arranged within a core subassembly and having a proximal end and a distal end and one or more windows through the core subassembly configured to allow electrical interface with the one or more connector blocks; and arranging one or more seal rings within the connector bore to interference fit within the connector bore and eliminate adulterant entry into the connector bore through the one or more windows.

In Example 11, the method of Example 10, wherein arranging the one or more seal rings within the connector bore includes arranging a first seal ring within the connector bore, and arranging the arranging one or more connector blocks within the connector bore includes a first connector block within the connector bore, and arranging the first seal ring within the connector bore occurs prior to arranging the first connector block within the connector bore.

In Example 12, the method of Example 11, wherein the one or more seal rings includes two seal rings and the one or more connector blocks includes one connector block, and the two seal rings are arranged on either side of the connector block.

In Example 13, the method of any one of Examples 10-11, wherein arranging the one or more connector block and arranging the one or more seal rings within the connector bore includes forming a first connector port subassembly and further comprising forming a second connector port subassembly by arranging one or more connector blocks within a second connector bore to interference fit within the connector bore and arranging one or more seal rings within the second connector bore to interference fit within the second connector bore.

In Example 14, the method of any one of Examples 10-12, further comprising forming a header of an implantable medical device by overmolding the connector port subassembly to a housing of an implantable medical device.

In Example 15, the method of Example 14, wherein forming the header includes overmolding the first connector port subassembly and the second connector port subassembly to a housing of an implantable medical device, with the first connector port subassembly being arranged above the second connector port subassembly.

In Example 16, a connector port subassembly for a medical device includes a core subassembly; a connector bore arranged within the core subassembly including a proximal end and a distal end; one or more connector blocks configured to interference fit within the connector bore; one or more windows through the core subassembly to the one or more connector blocks; and one or more seal rings configured to interference fit within the connector bore and eliminate adulterant entry into the connector bore through the one or more windows, the one or more seal rings having sidewalls, a first surface extending between the sidewalls, and a plurality of ridges arranged along the first surface and the sidewalls of the one or more seal rings configured to engage with an interior surface of the connector bore.

In Example 17, the connector port subassembly of Example 16, wherein a diameter of the interior surface of the connector bore is smaller than a diameter of the one or more seal rings.

In Example 18, the connector port subassembly of Example 16, wherein the one or more seal rings includes a first portion comprising a first material, and a second portion comprising a second material, and the first material is less flexible than the second material.

In Example 19, the connector port subassembly of Example 18, wherein the first material includes a high durometer and the second material includes a low durometer.

In Example 20, the connector port subassembly of Example 19, wherein the sidewalls and the first surface of the one or more seal rings comprise the first material.

In Example 21, the connector port subassembly of Example 16, wherein the connector bore includes a terminal pin cavity, and the core subassembly includes a window to the terminal pin and a projection configured to at least partially surround portions of a seal plug.

In Example 22, the connector port subassembly of Example 21, wherein the seal plug is captured within the connector bore producing an interference fit between the seal plug and the connector bore.

In Example 23, the connector port subassembly of Example 16, wherein the one or more seal rings includes two seal rings and the one or more connector blocks includes one connector block, and the two seal rings are arranged on either side of the connector block.

In Example 24, an implantable medical device includes a housing; and a header attached to the housing, the header including one or more connector port subassemblies, each of the one or more connector port subassemblies having: a connector bore arranged within the core subassembly including a proximal end and a distal end, one or more connector blocks configured to interference fit within the connector bore, one or more windows through the core subassembly to the one or more connector blocks; and one or more seal rings configured to interference fit within the connector bore and eliminate adulterant entry into the connector bore through the one or more windows.

In Example 25, the device of Example 24, wherein the one or more connector port subassemblies include a first connector port subassembly and a second connector port subassembly, overmolded to the housing.

In Example 26, the device of Example 24, wherein the one or more seal rings includes a first portion comprising a first material, and a second portion comprising a second material, and the first material is less flexible than the second material.

In Example 27, the device of Example 26, wherein the first material includes a high durometer and the second material includes a low durometer.

In Example 28, the device of Example 27, wherein the sidewalls and the first surface of the one or more seal rings comprise the first material.

In Example 29, the device of Example 24, wherein the one or more seal rings having sidewalls, a first surface extending between the sidewalls, and a plurality of ridges arranged along the first surface and the sidewalls of the one or more seal rings configured to engage with an interior surface of the connector bore.

In Example 30, a method of manufacturing one or more connector port subassemblies includes arranging one or more connector blocks within a connector bore to interference fit within the connector bore, the connector bore being arranged within a core subassembly and having a proximal end and a distal end and one or more windows through the core subassembly configured to allow electrical interface with the one or more connector blocks; and arranging one or more seal rings within the connector bore to interference fit within the within the connector bore and eliminate adulterant entry into the connector bore through the one or more windows.

In Example 31, the method of Example 30, wherein arranging the one or more seal rings within the connector bore includes arranging a first seal ring within the connector bore, and arranging the arranging one or more connector blocks within the connector bore includes arranging a first connector block within the connector bore, and arranging the first seal ring within the connector bore occurs prior to arranging the first connector block within the connector bore.

In Example 32, the method of Example 31, wherein the one or more seal rings includes two seal rings and the one or more connector blocks includes one connector block, and the two seal rings are arranged on either side of the connector block.

In Example 33, the method of Example 30, wherein arranging the one or more connector block and arranging the one or more seal rings within the connector bore includes forming a first connector port subassembly and further comprising forming a second connector port subassembly by arranging one or more connector blocks within a second connector bore to interference fit within the connector bore and arranging one or more seal rings within the second connector bore to interference fit within the second connector bore.

In Example 34, the method of Example 30, further including forming a header of an implantable medical device by overmolding the connector port subassembly to a housing of an implantable medical device.

In Example 35, the method of Example 34, wherein forming the header includes overmolding the first connector port subassembly and the second connector port subassembly to the housing of an implantable medical device, with the first connector port subassembly being arranged above or beside the second connector port subassembly.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
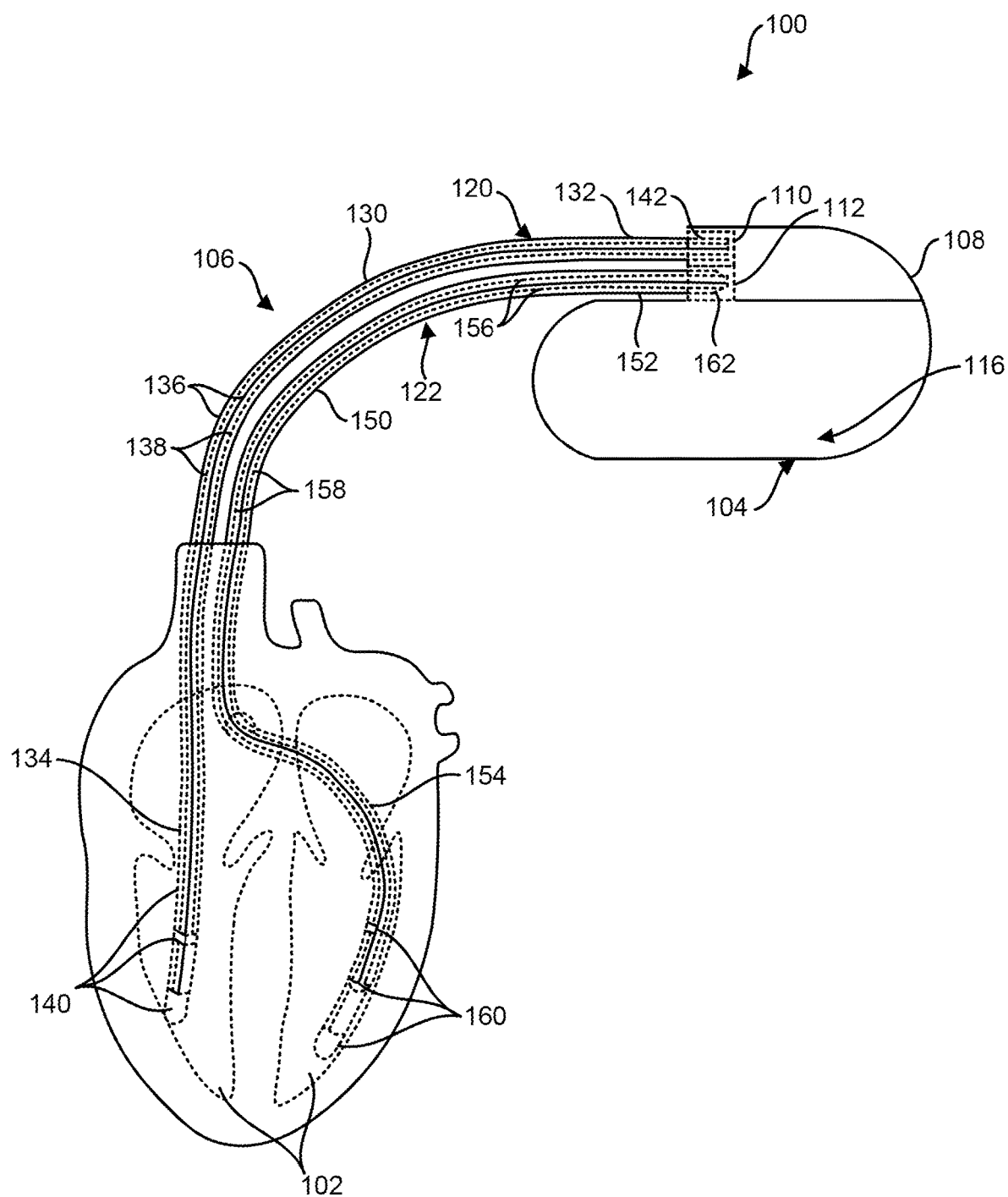
FIG. 1 is an illustration of an example implantable system for stimulating a target location on or within the heart, in accordance with various aspects of the present disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic illustration of an implantable system 100 for stimulating a target location 102 on or within the heart. As shown, the implantable system 100 includes an implantable medical device (IMD) 104 and an implantable lead assembly 106 connected to the IMD 104. In various embodiments, the IMD 104 is an implantable pulse generator adapted to generate electrical signals to be delivered to the target location 102 for pacing and/or for sensing electrical activity at a location on or within the heart. The IMD 104 can include microprocessors to provide processing, evaluation, and to deliver electrical shocks and pulses of different energy levels and timing for defibrillation, cardioversion, and pacing to a heart in response to cardiac arrhythmia including fibrillation, tachycardia, heart failure, and bradycardia. In other instances, the implantable system 100 can also be suitable for use with implantable electrical stimulators, such as, but not limited to, neuro-stimulators, skeletal stimulators, central nervous system stimulators, or stimulators for the treatment of pain.

The IMD 104 may include one or more connector ports 110, 112. In certain instances, the IMD (e.g., pulse generator 104) includes a header 108 with the connector port(s) 110, 112. As shown, for example, the header 108 includes a first connector port 110 and a second connector port 112. In addition, the implantable lead assembly 106 includes a first implantable lead 120 connected to the first connector port 110 and a second implantable lead 122 connected to the second connector port 112. In some instances, the implantable lead assembly 106 may also include a third implantable lead (not shown) and the header 108 may include a corresponding third connector port (not shown and up to five connector ports may be used). The IMD 104 also includes a housing 116 that is connected to the header 108. The housing 116 can include a source of power as well as electronic circuitry. The header 108 may be overmolded to the housing 116 and may be formed of a rigid polymer that is a non-conductive polymer such as, for example, an aromatic polyether-based thermoplastic polyurethane, polyether ether ketone, epoxy, or a polyethersulfone.

Each of the first and second implantable leads 120, 122 includes a flexible lead body, a plurality of conductor wires, a plurality of electrodes, and a terminal connector assembly. For example, as shown, the first implantable lead 120 includes a flexible lead body 130 having a proximal end 132, a distal end portion 134, and a plurality of conductor lumens 136 extending axially within the flexible lead body 130 from the proximal end 132 to the distal end portion 134. The first implantable lead 120 also includes a plurality of conductor wires 138, each conductor wire extending within one of the conductor lumens 136 in the flexible lead body 130. The first implantable lead 120 further includes a plurality of electrodes 140 coupled to the distal end portion 134 of the flexible lead body 130. Each of the electrodes 140 is electrically coupled to at least one of the plurality of conductor wires 138. The first implantable lead 120 also includes a terminal connector assembly 142 (or terminal pin) coupled to the proximal end 132 of the flexible lead body 130. The terminal connector assembly 142 is sized to be inserted into and received by the first connector port 110 of the header 108.

Similarly, the second implantable lead 122 includes a flexible lead body 150 having a proximal end 152, a distal end portion 154, and a plurality of conductor lumens 156 extending axially within the flexible lead body 150 from the proximal end 152 to the distal end portion 154. The second implantable lead 122 also includes a plurality of conductor wires 158, each conductor wire extending within one of the conductor lumens 156 in the flexible lead body 150. Further, the second implantable lead 122 includes a plurality of electrodes 160 coupled to the distal end portion 154 of the flexible lead body 150. Each of the electrodes 160 is electrically coupled to at least one of the plurality of conductor wires 158. The second implantable lead 122 also includes a terminal connector assembly 162 coupled to the proximal end 152 of the flexible lead body 150. The terminal connector assembly 162 is sized to be inserted into and received by the second connector port 112 of the header 108.

As an example of implant locations for one or more leads, the first implantable lead 120 is shown extending into a right ventricle of the heart, and the second implantable lead 122 extending through the coronary sinus and into a coronary vein disposed outside the left ventricle of the heart. The electrical signals and stimuli conveyed by the IMD 104 are carried to the electrode at the distal end of the lead by the conductors. The IMD 104 is typically implanted subcutaneously within an implantation location or pocket in the patient's chest or abdomen.

As shown in FIG. 1, the header 108 may include one or more connector port(s) 110, 112. Components arranged within the connector port(s) 110, 112 form a subassembly that differs based on the industry standard of the lead(s) 120, 122 that is to be inserted into the connector port(s) 110, 112. As described in further detail below, the various aspects of the present disclosure are configured to increase options in building the connector port 110, 112 subassemblies that are to be arranged within the header 108. The IMD 104 may use different standards with each of the different standards requiring different numbers electrical connections and/or multiple connector port subassemblies in the same header 108. As described in further detail below, the components and the connector port 110, 112 subassemblies allow for adaptability and adjustability in manufacture to lessen the number of pre-made connector port 110, 112 subassemblies needed to assemble headers 108 having connector port 110, 112 with various industry standards.

Figure 2:
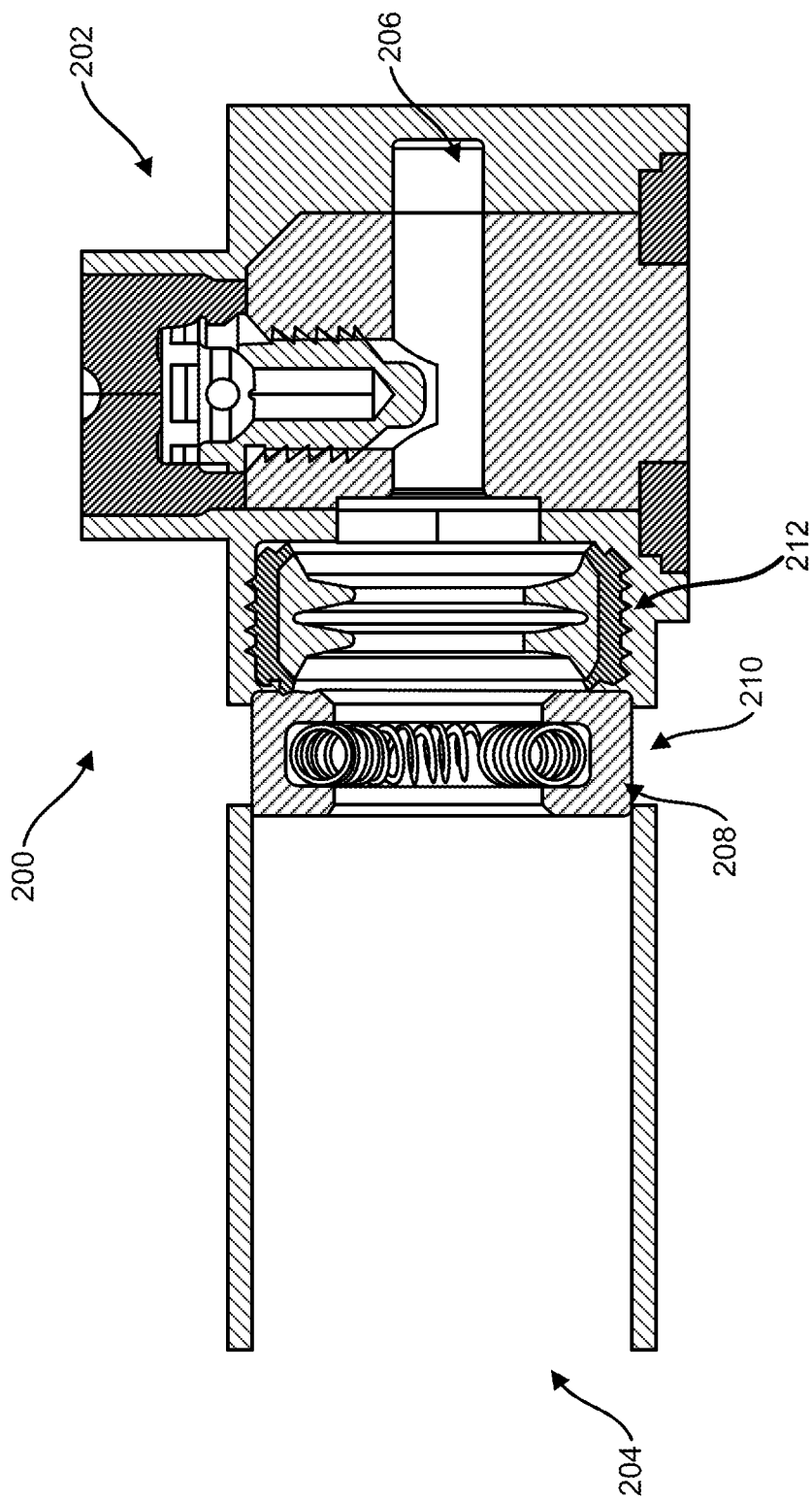
FIG. 2 is a cross-sectional view of an example connector port subassembly medical device, in accordance with various aspects of the present disclosure.

FIG. 2 is a cross-sectional view of an example connector port subassembly medical device, in accordance with various aspects of the present disclosure. A connector bore 202 is arranged within a core subassembly 200, and includes a proximal end 204 and a distal end 206. One or more connector blocks 208 are arranged within the connector bore 202. In addition, one or more windows 210 are arranged through the core subassembly 200 to allow for electrical connection to the one of more connector blocks 208 (e.g., from circuitry arranged within a housing of an implantable medical device as described above with reference to FIG. 1). One or more seal rings 212 are also arranged within the connector bore 202. The one or more seal rings 212 are configured to interference fit within the connector bore 202 and eliminate adulterant, contaminant, or unintended materials (e.g., epoxy, overmold) from entering the connector bore 202 (e.g., lead cavity or interior lumen or portion within the one or more connector blocks 208 and seal rings 212) through the one or more windows 210.

The core subassembly 200 may be arranged within a header 108 of an implantable medical device (as described above in detail with reference to FIG. 1). The header 108 is mountable to an implantable system 100 and an electrically conductive connector block 208 located within the header 108 (FIG. 1). The conductive connector block is formed from a substantially metallic material.

The core subassembly 200 may be overmolded to form a header, as described above with reference to FIG. 1. In certain instances, one or more core assemblies 200 may be overmolded to form the header. In addition and in certain instances, an adhesive or epoxy may be applied to the exterior of the one or more core assemblies 200 prior to overmolding. The one or more seal rings 212 are configured to eliminate adulterant, contaminant, or unintended materials (e.g., epoxy, overmold) contact with or entering the connector bore 202 (e.g., lead cavity) that exist due to the one or more windows 210 (e.g., electrically connect the connector blocks to components of the implantable medical device) between an exterior and an interior of the connector bore 202. The one or more seal rings 212 block overmold material and adhesive from entering the connector bore 302 and contacting connector blocks 208.

As described in further detail below, one or more connector blocks 208 and/or one or more seal rings 212 may be arranged within the connector bore 202. The number and structure of connector blocks 208 and/or seal rings 212 may be dependent on the industry standard desired for the core subassembly 200. As described in further detail below, the connector blocks 208 and/or seal rings 212 may be interference fit within the connector bore 202. The interference fit of the connector blocks 208 and/or seal rings 212 maintains the location of the connector blocks 208 and/or seal rings 212 within the connector bore 202. In this manner, the number and configuration of connector blocks 208 and/or seal rings 212 arranged within the connector bore 202, which may be specific one or more of the industry standards (e.g., IS-1, IS4, DF4), allows for multiple permutations of multiple subassemblies 200 (having different standards) together in one header. For example, the core subassembly 200 shown in FIG. 2 may be the IS-1 standard. In certain instances, an additional seal ring 212 is placed to surround the connector block 208 in this standard. The connector blocks 208 and/or seal rings 212 being configured as such allows for customization a connector assembly when multiple core subassemblies 200 (which may be of different standards) are arranged within a single connector assembly. In addition, the connector blocks 208 and/or seal rings 212 may have different configurations or structures and may be assembled within the connector bore 202 to comply with a desired standard.

Figure 3:
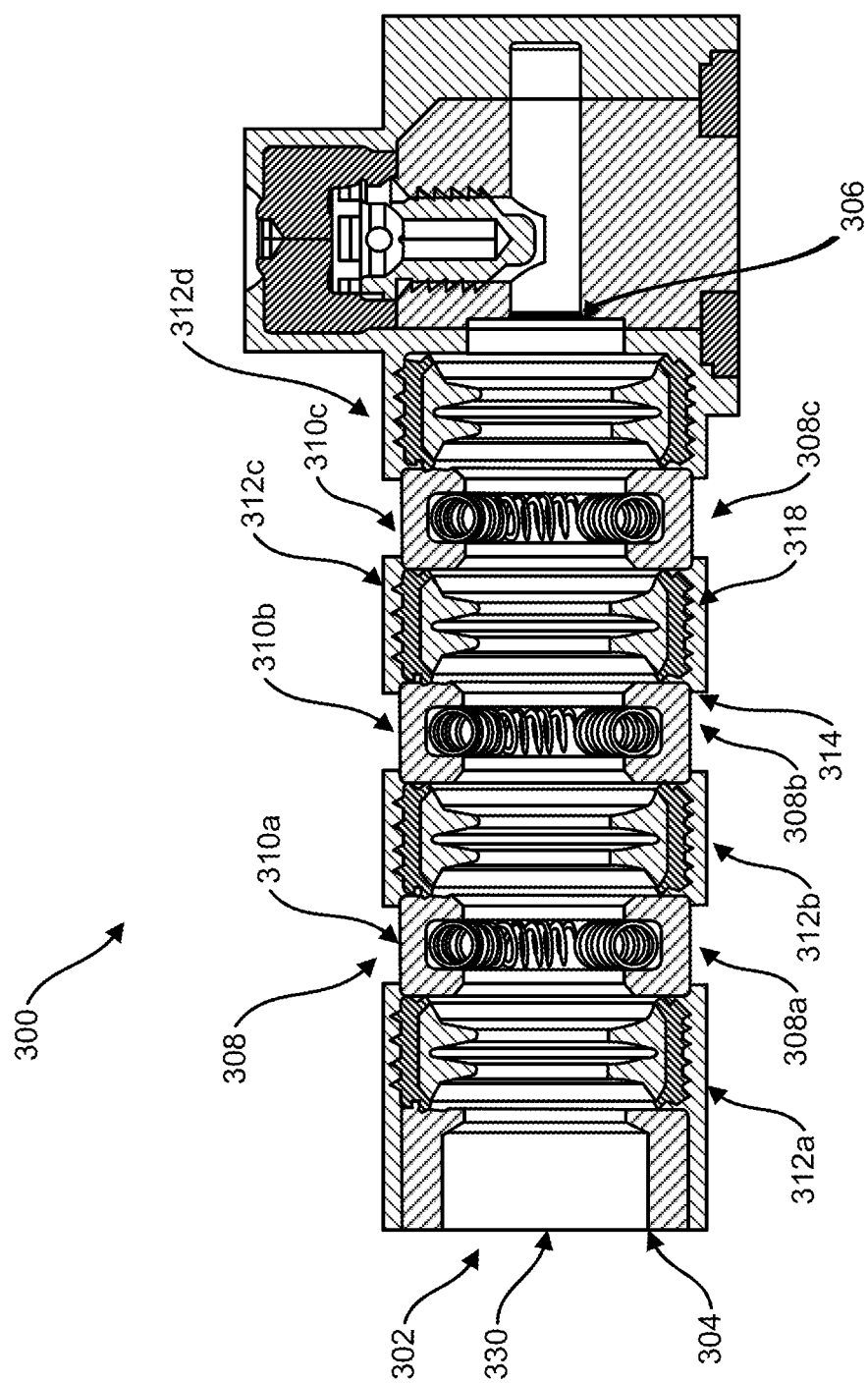
FIG. 3 is a cross-sectional view of another example connector port subassembly medical device, in accordance with various aspects of the present disclosure.

FIG. 3 is a cross-sectional view of another example connector port subassembly medical device, in accordance with various aspects of the present disclosure. The subassembly medical device includes a core subassembly 300, which may be formed from a rigid polymer that is a non-conductive polymer, and a connector bore 302, having a proximal end 304 and a distal end 306, arranged within the core subassembly 300. In addition, one or more connector blocks 308 and one or more seal rings 312 are arranged within the connector bore 302. In certain instances, the connector blocks 308 and/or the seal rings 312 are configured to interference fit within the connector bore 302.

The one or more seal rings 312 and one or more connector blocks 308 may be arranged between the proximal end 304 and distal end 306 of the connector bore 302. In certain instances and as shown, the seal rings 312 include a plurality of seal rings 312a, 312b, 312c and 312d and the one or more connector blocks 308 includes a plurality of connector blocks 308a, 308b, 308c. The number of connector blocks 308a, 308b, 308c and seal rings 312a, 312b, 312c and 312d is dependent on the industry standard desired for the core subassembly 300. As shown, the core subassembly 300 includes three connector blocks 308a, 308b, 308c separated by four seal rings 312a, 312b, 312c and 312d. FIG. 3, for example, shows a connector port subassembly that may be used for the IS-4 and DF-4 standards.

In certain instances, the connector blocks 308a, 308b, 308c and seal rings 312a, 312b, 312c and 312d are configured to interference fit within the connector bore 302. In certain instances, the diameter of an interior surface 314 of the connector bore 302 is smaller than the diameter of the connector blocks 308a, 308b, 308c and/or seal rings 312a, 312b, 312c and 312d. The connector blocks 308a, 308b, 308c and seal rings 312a, 312b, 312c and 312d being configured to interference fit within the connector bore 302 allows for the placement tolerance required for alignment of the connector blocks 308a, 308b, 308c to interface with corresponding conductors on a lead that is to be inserted within the interior bore between the connector blocks 308a, 308b, 308c and seal rings 312a, 312b, 312c and 312d. The core subassembly 300 may be formed of a material (e.g., a thermoplastic) that is configured to yield enough to allow for arrangement of the connector blocks 308a, 308b, 308c and seal rings 312a, 312b, 312c and 312d within the connector bore 302.

In certain instances, the connector blocks 308a, 308b, 308c and seal rings 312a, 312b, 312c and 312d may be pressed into a desired position within the connector bore 302 at the locations needed to interface with corresponding conductors on a lead that is to be inserted into the connector bore 302. Each of the connector blocks 308a, 308b, 308c and seal rings 312a, 312b, 312c and 312d may be separately arranged within the connector bore 302. In certain instances and in the configuration shown, a first seal ring 312d may be arranged within the connector bore 302 prior to a first connector block 308c. In addition, a second seal ring 312c may be arranged within the connector bore 302 such that two seal rings 312c, 312d are arranged on either side of the connector block 308c.

In certain instances, the seal rings 312a, 312b, 312c and 312d include a plurality of ridges 318 arranged along an exterior surface (contact the interior surface 314 of the connector bore 302) and sidewalls of the connector blocks 308a, 308b, 308c. The plurality of ridges 318 along the sidewalls (as discussed in further detail below with reference to FIG. 4) contact side portions of the connector blocks 308a, 308b, 308c. The core subassembly 300 includes one or more windows 310a, 310b, 310c arranged through the core subassembly 300 to the one or more connector blocks 308. The plurality of ridges 318 may be configured to eliminate adulterant, contaminant, or unintended materials (e.g., epoxy, overmold) from contact with or entering the connector bore 302 (e.g., lead cavity within the connector blocks 308a, 308b, 308c and seal rings 312a, 312b, 312c and 312d) by way of or through the one or more windows 310a, 310b, 310c. The plurality of ridges 318 are configured to seal out material, for example, when the core subassembly 300 is overmolded to form a header of an implantable medical device.

In certain instances and as shown in FIG. 1, the header may include multiple connectors for leads. In these instances, multiple core subassemblies 300, that include the connector blocks 308a, 308b, 308c and seal rings 312a, 312b, 312c and 312d, may be overmolded together. In certain instances, the core assemblies 300 within the same header may include different configurations and numbers of the connector blocks 308a, 308b, 308c and seal rings 312a, 312b, 312c and 312d when compared to one another. In this manner, the implantable medical device may include a header formed of the same connector blocks 308a, 308b, 308c and seal rings 312a, 312b, 312c and 312d and have connector ports for leads that comply with different industry standards. The header may include a first subassembly 300 and a second subassembly 300 (or additional subassemblies 300). In certain instances, forming the header includes overmolding the first connector port subassembly 300 and the second connector port subassembly 300 to a housing of an implantable medical device, with the first connector port subassembly 300 being arranged above the second connector port subassembly 300 (e.g., as shown in FIG. 1) or beside the second connector port subassembly 300.

In certain instances, the core subassembly 300 is configured to stretch to allow for the outer diameter of the connector bore 302 to enlarge. When multiple core subassemblies 300 (e.g., two, three, four, five) are stacked together to form a header, the connector bore 302 diameter may be altered. To prevent interference between adjacent connector bore subassemblies 300, the connector bore 302 diameter can be reduced or enlarged in targeted areas to allow for core subassembly outer diameter to stretch above the areas with connector blocks 308 without protruding outside the greater envelope of connector bore 300 outer diameter.

The core subassembly 300 (or core assemblies 300), by way of the connector blocks 308a, 308b, 308c and seal rings 312a, 312b, 312c and connector bore 302, reduces the number of subassemblies required in complying with different patient device configuration needs. The connector blocks 308a, 308b, 308c and seal rings 312a, 312b, 312c allow for customizable arrangements when combining subassemblies 300 into different configurations. The connector blocks 308a, 308b, 308c and seal rings 312a, 312b, 312c being configured to interference fit within the connector bore 302 lessens the additive tolerance stack-up values between the components such that the connector blocks 308a, 308b, 308c and seal rings 312a, 312b, 312c may be placed within the connector bore 300 independently to lessen error between the components as compared to if the connector blocks 308a, 308b, 308c and seal rings 312a, 312b, 312c were assembled together. In addition, the connector blocks 308a, 308b, 308c and seal rings 312a, 312b, 312c are configured to interference fit prior to overmolding. When the overmold is placed, the core subassembly 300 is resistant to leakage as opposed to containing any windows allowing for leakage into interior or bore of the core subassembly 300. The location of each of the connector blocks 308a, 308b, 308c is not dependent on the neighboring seal rings 312a, 312b, 312c for location. The locations of the connector blocks 308a, 308b, 308c in the bore may be determined by the insertion depth during the assembly process. A retaining sleeve 330 may be arranged adjacent a proximal most one of the seal rings 312c, as shown. In other instances, the retaining sleeve 330 may be arranged adjacent a proximal most one of connector blocks 308c. In either instance, the retaining sleeve 330 is arranged proximal to each of the connector blocks 308a, 308b, 308c and seal rings 312a, 312b, 312c. The retaining sleeve 330 may facilitate maintaining a position of the connector blocks 308a, 308b, 308c and seal rings 312a, 312b, 312c within the connector bore 302.

Figure 4:
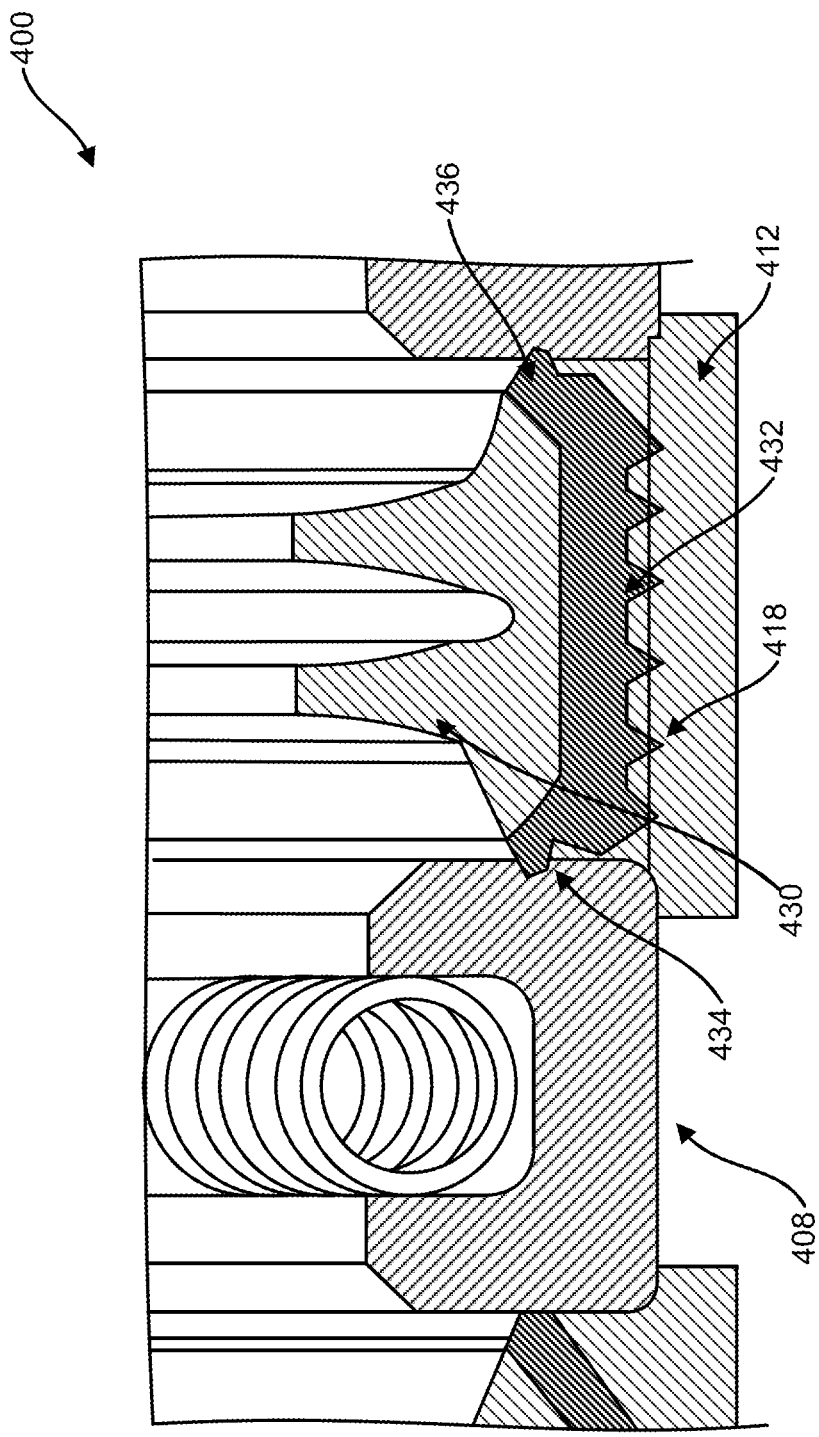
FIG. 4 is a close-up cross-sectional view of a portion of an example connector port subassembly medical device, in accordance with various aspects of the present disclosure.

FIG. 4 is a close-up cross-sectional view of a portion of an example connector port subassembly medical device, in accordance with various aspects of the present disclosure. As shown in FIG. 4, the subassembly medical device shown includes a core subassembly 400 and a connector block 408 adjacent a seal rings 412 (which may be configured to interference fit within a connector bore as described in detail above).

The seal ring 412 includes a first surface 430, a second surface 432, and sidewalls 434, 436. The second surface 432 may be configured to contact an interior lumen of a connector bore. The sidewalls 434, 436, which may be angled outwardly from the second surface 432, may be configured to contact adjacent components arranged within the connector bore. For example and as is shown, one of the sidewalls 434, 436 is configured to contact the connector block 408. In certain instances, the seal ring 412 includes a plurality of ridges 418 arranged along the second surface 432 and the sidewalls 434, 436. The ridges 418 on the sidewalls 434, 436 are configured to contact side portions of an adjacent connector block 308. In certain instances, the ridges 418 on the sidewalls 434, 436 block substances (e.g., adhesive, overmolding) from entering the connector bore. The ridges 418 on the sidewalls 434, 436, for example, may be configured eliminate adulterant, contaminant, or unintended materials (e.g., epoxy, overmold) from contact with or entering the connector bore (e.g., lead cavity) through the one or more windows. The plurality of ridges 418 are configured to seal out material, for example, when the core subassembly 300 is overmolded to form a header of an implantable medical device.

In certain instances, the seal ring 412 may include a first portion and a second portion with the first portion including a first material and the second portion including a second material. In certain instances, the first material is less flexible than the second material. More specifically, the first material may include a high durometer and the second material includes a low durometer. In certain instances, the sidewalls 434, 436 and the second surface 432 may be formed of the first material and the first surface 430 may be formed of the second material.

Figure 5:
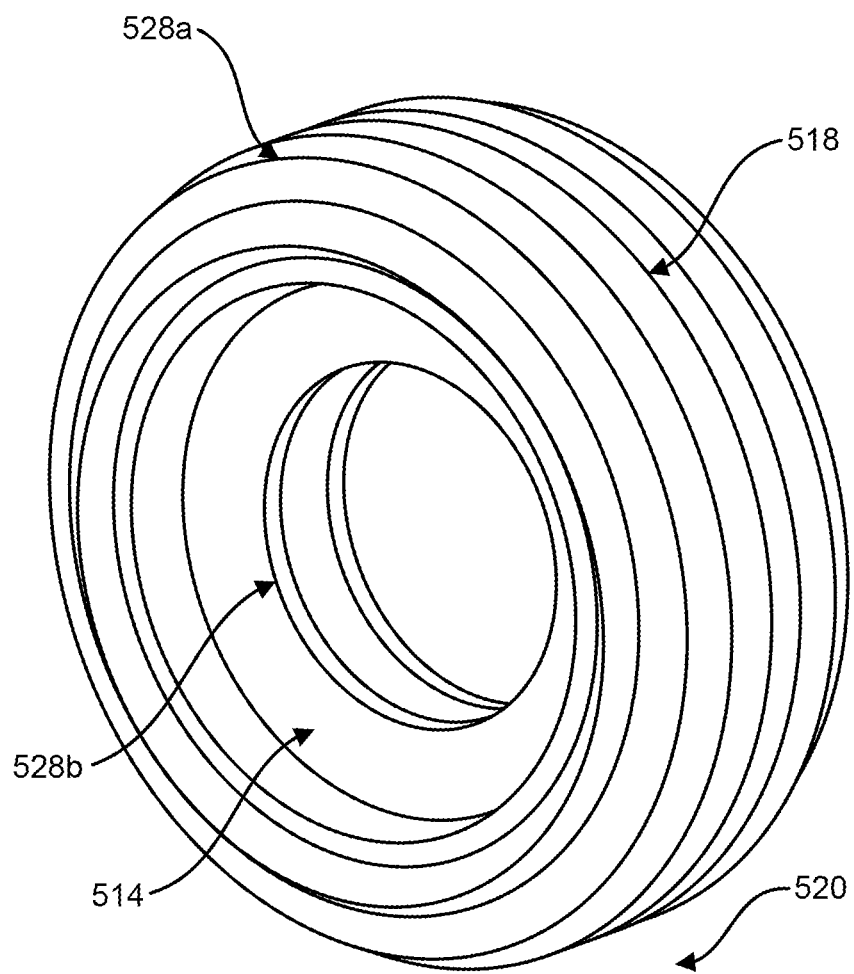
FIG. 5 is a perspective view of an example seal ring, in accordance with various aspects of the present disclosure.

FIG. 5 is a perspective view of an example seal ring 520, in accordance with various aspects of the present disclosure. As shown, the seal ring 520 includes a plurality of ridges 528 (which can also be a singular structure) on an inner surface 514 and an outer surface 518. In certain instances, exterior ridges 528a are spaced closer together than interior ridges 528b. In addition, the exterior ridges 528a may include less height or depth than the interior ridges 528b.

In certain instances, the exterior ridges 528a (or structures) may be formed of a material having a first durometer and the interior ridges 528b (or structures) may be formed of a material having a second durometer. The second durometer may have a greater flexibility than the first durometer. The interior ridges 528b may have a flexibility that allows for lead insertion while the exterior ridges 528a may facilitate an interference fit within a connector bore as described in detail above.

Figure 6A:
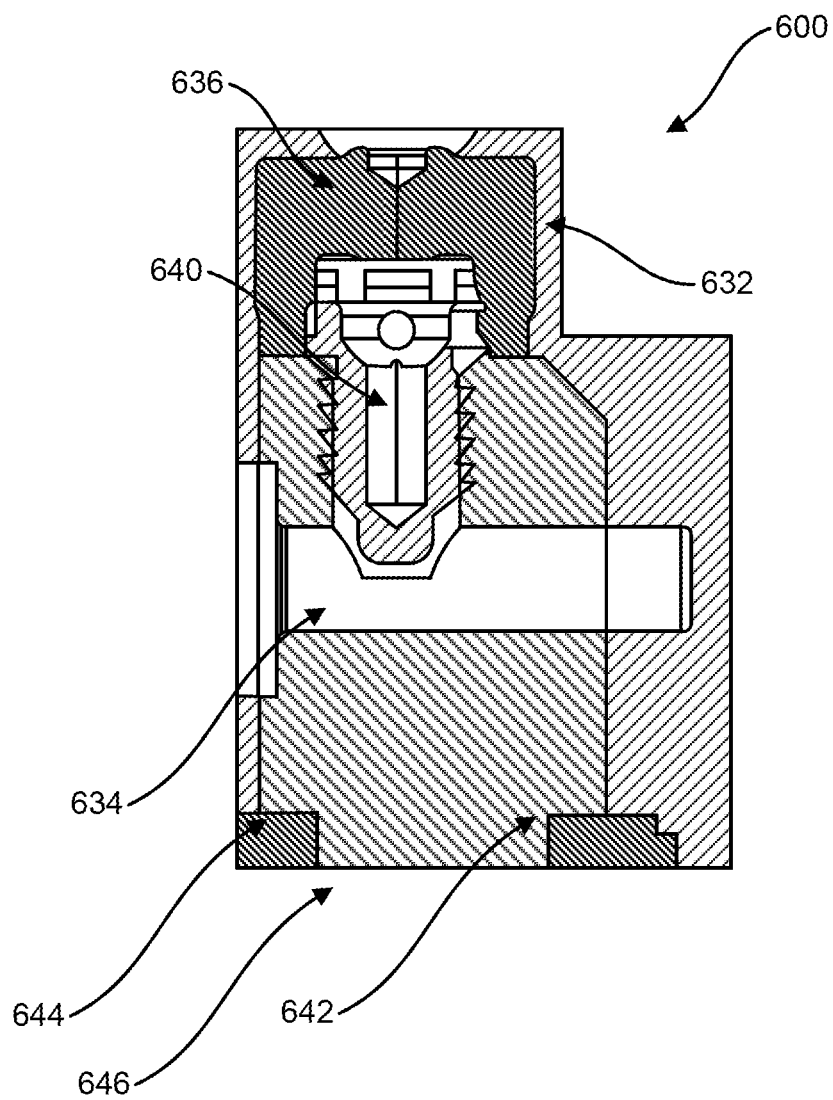
FIG. 6A is close-up cross-sectional side view of an example connector port subassembly medical device and seal plug, in accordance with various aspects of the present disclosure.

FIG. 6A is close-up side view of an example connector port subassembly medical device and seal plug 636, in accordance with various aspects of the present disclosure. A terminal pin cavity 634 portion of a core subassembly 600 is shown in FIG. 6A. The core subassembly 600 includes a window (as described in FIG. 6B) to the terminal pin cavity 634 that a set screw 640 is arranged within. The core subassembly 600 also includes a projection 632 configured to at least partially surround portions of a seal plug 636. As opposed to inserting the seal plug 636 into the core subassembly 600 and sealing the seal plug 636 within the core subassembly 600 with an adhesive, the projection 632 captures the seal plug 636 within the core subassembly 600. The projection 632 at least partially surrounds the seal plug 636. The seal plug 636 may allow for adjustment of the set screw 640 to hold a terminal pin of a lead in place within the core subassembly 600. Also shown is a terminal pin connector block 642. A seal ring 644 is also arranged about the terminal pin connector block 642, which is configured to keepout overmold material and leave a weld window 646 for wire attachment.

Figure 6B:
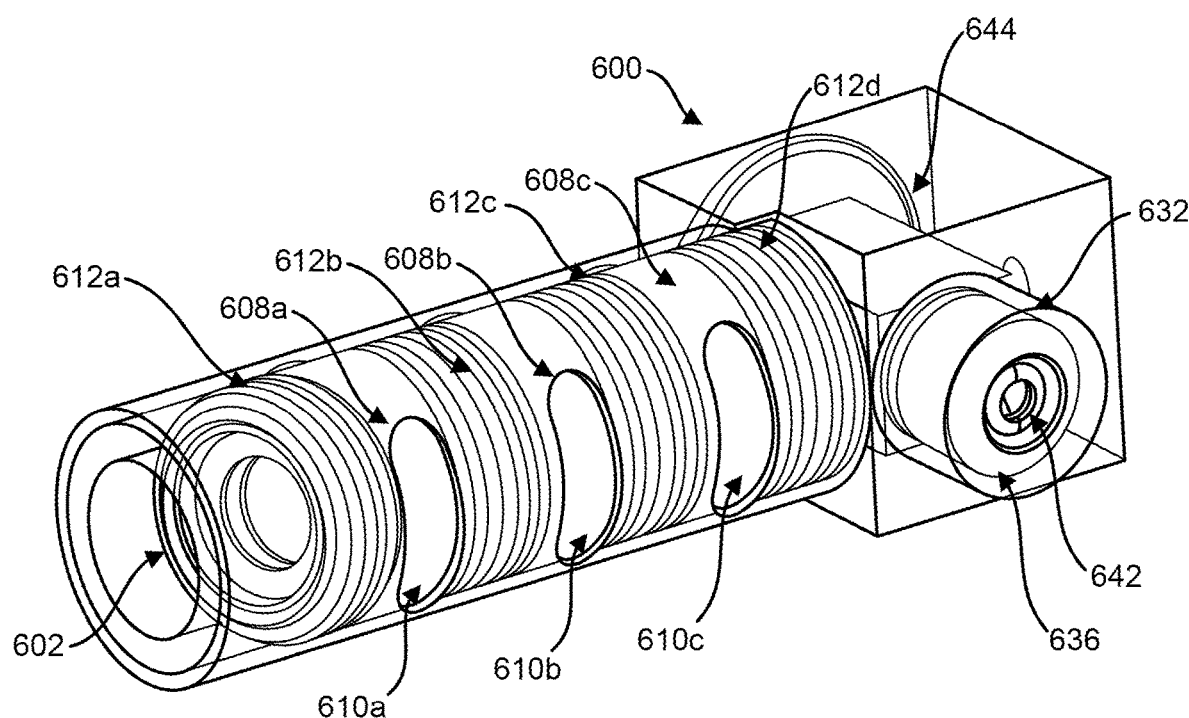
FIG. 6B is an perspective partially transparent view of the core subassembly and the seal plug, shown in FIG. 6A, in accordance with various aspects of the present disclosure.

FIG. 6B is a perspective partially transparent view of the core subassembly 600 and the seal plug 636, shown in FIG. 6A, in accordance with various aspects of the present disclosure. The core subassembly 600 is shown along with a connector bore 602 and windows 610a, 610b, 610c through the core subassembly 600 to connector blocks 608a, 608b, 608c. As discussed in detail above, the core subassembly 600 may also include seal rings 612a, 612b, 612c and 612d are configured to interference fit within the connector bore 602 and arranged between and separating the connector blocks 608a, 608b, 608c from one another. The seal rings 612a, 612b, 612c and 612d may be formed of an insulative material. As also discussed in detail above, the seal rings 612a, 612b, 612c and 612d are configured to eliminate adulterant contact with or entering the connector bore 602 through the one or more windows 610a, 610b, 610c.

As shown in FIG. 6B, the projection 632 captures the seal plug 636 within the core subassembly 600. The projection 632 at least partially surrounds the seal plug 636. The seal plug 636 includes a window 642 through which a tool (e.g., wrench) may be inserted to adjust the set screw 640. The seal plug 636 is configured to protect against errant wrench blade insertions and seal out material or fluids from entering the terminal pin cavity 634.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A connector port subassembly for a medical device, the connector port subassembly comprising:
a core subassembly;
a connector bore arranged within the core subassembly including a proximal end and a distal end;
one or more connector blocks configured to interference fit within the connector bore;
one or more windows through the core subassembly to the one or more connector blocks; and
one or more seal rings configured to interference fit within the connector bore and eliminate adulterant entry into the connector bore through the one or more windows,
wherein the one or more seal rings each include an exterior portion having an exterior surface for contacting the connector block, and an interior portion having an interior surface for coupling with the medical device, wherein the exterior surface includes a plurality of ridges configured to engage with an interior surface of the connector bore,
wherein the exterior surface of each of the one or more seal rings comprises a first material and the interior portion of each of the one or more seal rings comprises a second material, the first material being less flexible than the second material.

2. The connector port subassembly of claim 1, wherein a diameter of the interior surface of the connector bore is smaller than a diameter of the one or more seal rings.

3. The connector port subassembly of claim 1, wherein the first material includes a first durometer and the second material includes a second durometer, and wherein the first durometer is greater than the second durometer.

4. The connector port subassembly of claim 1, wherein the exterior surface includes sidewalls and a first surface both of which include at least one exterior facing ridge.

5. The connector port subassembly of claim 1, wherein the connector bore includes a terminal pin cavity, and the core subassembly includes a window to a terminal pin and a projection configured to at least partially surround portions of a seal plug, the seal plug being captured within the connector port subassembly by the projection.

6. The connector port subassembly of claim 5, wherein the seal plug is captured within the connector bore producing an interference fit between the seal plug and the connector bore.

7. The connector port subassembly of claim 1, wherein the one or more seal rings includes two seal rings and the one or more connector blocks includes one connector block, and the two seal rings are arranged on either side of the connector block.

8. The connector port subassembly of claim 1, wherein the connector port subassembly is capable of being overmolded to form a header.

9. An implantable medical device comprising:
a housing; and
a header attached to the housing, the header including one or more connector port subassemblies, each of the one or more connector port subassemblies having:
a connector bore arranged within a core subassembly including a proximal end and a distal end,
one or more connector blocks configured to interference fit within the connector bore,
one or more windows through the core subassembly to the one or more connector blocks; and
one or more seal rings configured to interference fit within the connector bore and eliminate adulterant entry into the connector bore through the one or more windows, the seal rings including an exterior portion having an exterior surface associated with an outer diameter of the seal ring and a interior portion having an interior surface associated with an inner diameter of the seal ring, wherein the exterior surface comprises a first material and the interior portion comprises a second material, wherein the first material is less flexible than the second material.

10. The device of claim 9, wherein the one or more connector port subassemblies include a first connector port subassembly and a second connector port subassembly, overmolded to the housing.

11. The device of claim 9, wherein the first material includes a first durometer and the second material includes a second durometer, and wherein the first durometer is greater than the second durometer.

12. The device of claim 9, wherein the one or more seal rings have sidewalls, a first surface extending between the sidewalls, and a plurality of ridges arranged along the first surface and the sidewalls of the one or more seal rings configured to engage with an interior surface of the connector bore.

13. A method of manufacturing one or more connector port subassemblies, method comprising:

arranging one or more connector blocks within a connector bore to interference fit within the connector bore, the connector bore being arranged within a core subassembly and having a proximal end and a distal end and one or more windows through the core subassembly configured to allow electrical interface with the one or more connector blocks; and arranging one or more seal rings within the connector bore to interference fit within the connector bore and eliminate adulterant entry into the connector bore through the one or more windows, wherein the one or more seal rings are configured to engage with an interior surface of the connector bore, the seal rings having a first portion including sidewalls, a first outer surface extending between the sidewalls, and a plurality of ridges arranged along the first outer surface and the sidewalls, the first outer surface comprising a first material, and wherein the one or more seal rings are configured to engage with a terminal pin of an implantable lead, the seal ring having a second portion including an inner surface extending between the sidewalls, the second portion comprising a second material, wherein the first material is less flexible than the second material.

14. The method of claim 13, wherein arranging the one or more seal rings within the connector bore includes arranging a first seal ring within the connector bore, and arranging the one or more connector blocks within the connector bore includes arranging a first connector block within the connector bore, and arranging the first seal ring within the connector bore occurs prior to arranging the first connector block within the connector bore.

15. The method of claim 14, wherein the one or more seal rings includes two seal rings and the one or more connector blocks includes one connector block, and the two seal rings are arranged on either side of the connector block.

16. The method of claim 13, wherein arranging the one or more connector block and arranging the one or more seal rings within the connector bore includes forming a first connector port subassembly and further comprising forming a second connector port subassembly by arranging one or more connector blocks within a second connector bore to interference fit within the connector bore and arranging one or more seal rings within the second connector bore to interference fit within the second connector bore.

17. The method of claim 13, further comprising forming a header of an implantable medical device by overmolding the one or more connector port subassemblies to a housing of the implantable medical device.

18. The method of claim 17, wherein forming the header includes overmolding a first connector port subassembly and a second connector port subassembly to the housing, with the first connector port subassembly being arranged above or beside the second connector port subassembly.

\* \* \* \* \*